United States Patent [19]

Lazarus et al.

[11] Patent Number: 5,583,025
[45] Date of Patent: *Dec. 10, 1996

[54] ENZYMES FOR THE PRODUCTION OF 2-KETO-L-GULONIC ACID

[75] Inventors: Robert A. Lazarus, Millbrae, Calif.; Mark Hurle, Bridgeport, Pa.; Stephen Anderson, Princeton; David B. Powers, Somerset, both of N.J.

[73] Assignee: Rutgers, The State University of New Jersey, Piscataway, N.J.

[*] Notice: The term of this patent shall not extend beyond the expiration date of Pat. No. 5,376,544.

[21] Appl. No.: 249,377

[22] Filed: May 24, 1994

Related U.S. Application Data

[63] Continuation of Ser. No. 941,414, Sep. 8, 1992, Pat. No. 5,376,544.

[51] Int. Cl.$^6$ ........................................................ C12N 9/04
[52] U.S. Cl. .................... 435/190; 435/189; 435/69.1; 435/172.3; 435/320.1; 435/252.3; 435/252.33; 536/23.2; 930/240; 935/10; 935/14
[58] Field of Search ................................ 435/189, 172.3, 435/320.1, 252.3, 252.33; 536/23.2; 935/10, 14; 930/240

[56] References Cited

U.S. PATENT DOCUMENTS

| | | | |
|---|---|---|---|
| Re. 30,872 | 2/1982 | Sonoyamas et al. | 435/138 |
| 3,959,076 | 5/1976 | Sonoyama et al. | 435/138 |
| 3,998,697 | 12/1976 | Sonoyama et al. | 435/42 |
| 4,543,331 | 9/1985 | Sonoyama et al. | 435/138 |
| 4,757,012 | 7/1988 | Estell et al. | 435/172.3 |
| 4,758,514 | 7/1988 | Light et al. | 435/91.41 |
| 4,945,052 | 7/1990 | Hardy et al. | 435/172.3 |
| 5,004,690 | 4/1991 | Light et al. | 435/138 |
| 5,008,193 | 4/1991 | Anderson et al. | 435/138 |
| 5,017,691 | 5/1991 | Lee et al. | 530/351 |
| 5,032,514 | 7/1991 | Anderson et al. | 435/138 |
| 5,376,544 | 12/1994 | Lazarus et al. | 435/190 |

FOREIGN PATENT DOCUMENTS

| | | |
|---|---|---|
| 046284 | 8/1981 | European Pat. Off. . |
| 088409 | 3/1983 | European Pat. Off. . |
| 142169 | 11/1984 | European Pat. Off. . |

OTHER PUBLICATIONS

Miller, J. V. et al., "Purification and Characterization of 2,5-Diketo–D–Gulonate Reductase from Corynebacterium Sp.," *J. Biol. Chem.* 262:9016–9020 (1987).

Nicholson, H. et al., "Enhanced Protein Thermostability from Designed Mutations that Interact with α–Helix Dipoles," *Nature* 336:651–656 (1988).

Rastetter, W. H., "Enzyme Egineering: Applications and Promise," *Trends Biotechnol.* 1:80–84 (1983).

Richardson, J. S. et al., "Amino Acid Preferences for Specific Locations at the Ends of α–Helices," *Science* 240:1648–1652 (1988).

Sonoyama, T. et al., "Purification and Properties of Two 2,5 Diketo–D–Gluconate Reductases from a Mutant Strain Derived from Corynebacterium sp.," *J. Ferment. Technol.* 65:311–317 (1987).

Sonoyama, T. et al., "Distribution of Microorganisms Capable of Reducing 2,5 Diketo–D–Gluconate to 2–Keto–L–Gulonate," *Agric. Biol. Chem.* 51:2003–2004 (1987).

Sonoyama, T. et al., "Production of 2–Keto–L–Gulonic Acid from D–Glucose by Two Stage Fermentation," *Appl. Environ. Microbiol.* 43:1064–1069 (1982).

Wells, J. A. et al., "Recruitment of Substrate–Specificity Properties from One Enzyme into a Related One by Protein Engineering," *Proc. Natl. Acad. Sci.* (U.S.A.) 84:5167–5171 (1987).

Wilkinson, A. J. et al., "A Large Increase in Enzyme–Substrate Affinity by Protein Engineering," *Nature* 307:187–188 (1984).

Anderson, S. et al., "Production of 2–Keto–L–Gulonate, and Intermediate in L–Ascorbate Synthesis, by a Genetically Modified Erwinia herbicola," *Science* 230:144–149 (1985).

Grindley, J. F. et al., "Conversion of Glucose to 2–Keto–L–Gulonate, and Intermediate in L–Ascorbate Synthesis by a Recombinant Strain of *Erwinia citreus*," *Appl. Environ. Microbiol.* 54:1770–1775 (1988).

Kellis, J. T. et al., "Contribution of Hydrophobic Interactions to Protein Stability," *Nature* 333:784–786 (1988).

Imanaka, T. et al., "A New Way of Enhancing the Thermostability of Proteases," *Nature* 324:695–697 (1986).

Matthews, B. W. et al., "Enhanced Protein Thermostability from Site–Directed Mutations that Decreases the Entropy of Unfolding," *Proc. Natl. Acad. Sci.* (U.S.A.) 84:6663–6667 (1987).

Matsumura, M. et al., "Substantial Increase of Protein Stability by Multiple Disulphide Bonds," *Nature* 342:291–293 (1989).

Schulz et al. 1979 (9th Printing) in *Principles of Protein Structures* Springer Verlag, New York, pp. 171–175.

*Primary Examiner*—Christopher S. F. Low
*Attorney, Agent, or Firm*—Howrey & Simon; Jeffrey I. Auerbach

[57] ABSTRACT

Mutants of 2,5-diketo-D-gluconic acid reductase A, an enzyme used to produce 2-keto-L-gulonic acid, a precursor of ascorbic acid (vitamin C) are prepared by site-directed mutagenesis. These mutants have increased catalytic activity, increased expression levels, and/or enhanced temperature stability.

9 Claims, 3 Drawing Sheets

ENZYMES FOR THE PRODUCTION OF 2-KETO-L-GULONIC ACID

CROSS-REFERENCE TO RELATED APPLICATIONS

This application is a continuation of U.S. patent application Ser. No. 07/941,414 (filed on Sep. 8, 1992) now U.S. Pat. No. 5,376,544 Dec. 27, 1994.

FIELD OF THE INVENTION

The present invention relates to improved mutant forms of an industrially valuable enzyme as a result of site-directed mutagenesis. More specifically, the invention relates to mutated forms of 2,5-diketo-D-gluconic acid (2,5-DKG) reductase A, a naturally occurring variant of DKG reductase. The mutated forms show improved catalytic activity for converting 2,5-DKG stereoselectively into 2-keto-L-gulonic acid (2-KLG), a precursor of ascorbic acid (vitamin C). In addition, the mutated forms have increased in-vivo expression levels and/or improved temperature stability.

BACKGROUND OF THE INVENTION

Due to the expanding health consciousness of people around the world, there has been an increasing demand for vitamin C. Also contributing to the demand for ascorbic acid is its widespread use as an antioxidant for preserving food. One approach for satisfying this demand is to achieve increased production of 2-KLG, an intermediate in the production of ascorbic acid. The intermediate, 2-KLG, can be easily converted to ascorbic acid through acid or base catalyzed cyclization. It also has a greater stability and shelf life than ascorbic acid. Therefore, rather than producing ascorbic acid directly, it is more practical to stockpile 2-KLG for subsequent conversion to ascorbic acid.

A number of species of a first group of microorganisms, Erwinia, Acetobacter, and Gluconobacter, can produce 2,5-DKG from D-glucose. A second group of microorganisms from the coryneform group of bacteria (Corynebacterium, Brevibacterium, and Arthrobacter) as well as species of Micrococcus, Staphylococcus, Pseudomonas, Bacillus, and Citrobacter are capable of converting 2,5-DKG, produced by a microorganism of the first group, to 2-KLG. This cofermentation of appropriate microorganisms to produce 2-KLG was simplified by combining the relevant traits of both the *Erwinia sp.* and the *Corynebacterium sp.* in a single microorganism (Anderson et al., Science 23: 144–149 (1985)). This was accomplished by identifying the 2,5-DKG reductase in the *Corynebacterium sp.* that converts 2,5-DKG into 2-KLG. The gene for this reductase was then cloned and expressed in *Erwinia herbicola*, a bacterium of the family Enterobacteriaceae that converts D-glucose into 2,5-DKG in a single fermentation. The resulting recombinant bacterial strain, with 2,5-DKG reductase as the pivotal enzyme, was able to convert D-glucose into 2-KLG in a single-fermentation process (Lazarus et al. Fourth ASM Conf. Genet. Molec. Biol. Indust. Microorg., 187–193 (1989)).

Improving the catalytic efficiency of 2,5-DKG reductase, in the single-fermentation process, is a significant way to increase the production of 2-KLG. Also, a purified 2,5-DKG reductase A with increased catalytic activity could be used in an in vitro process for the conversion of 2,5-DKG to 2-KLG. For example, such a process would permit continuous production of 2-KLG through immobilization of the purified enzyme on a solid support.

According to the Michaelis-Menten scheme set out below, the

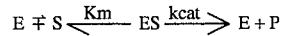

efficiency of an enzymatic reaction can be measured by two kinetic parameters, kcat and Km. The catalytic rate constant, kcat, also known as the turnover number, is a measure of the breakdown of the enzyme-substrate (ES) complex. It also represents the maximum number of substrate molecules (S) converted to product (P) via an ES complex per active site of the enzyme (E) per unit time. Vmax is the maximal velocity or rate of the enzyme catalyzed reaction when the enzyme is saturated with substrate. Therefore, Vmax is constant at saturating substrate concentration and remains unchanged with any increase in substrate concentration. The kcat at saturating substrate concentrations is related to Vmax and the total enzyme concentration, $[E_T]$, by the following equation: Vmax=kcat $[E_T]$. The Michaelis constant, Km, is equal to the dissociation constant of the ES complex. Therefore, Km is a measure of the strength of the ES complex. In a comparison of Km's, a lower Km represents a complex with a stronger, more favorable binding, while a higher Km represents a complex with a weaker, less favorable binding. The ratio, kcat/Km, called the specificity constant, represents the specificity of an enzyme for a substrate, i.e., the catalytic efficiency per enzyme molecule for a substrate. The larger the specificity constant, the more preferred the substrate is by the enzyme.

Impressive yields of 2-KLG have been achieved with a Corynebacterium 2,5-DKG reductase (2,5-DKG reductase A, also known as 2,5-DKG reductase II) (Anderson et al., Science 230: 144–149 (1985); Miller et al., J. Biol. Chem. 262: 9016 (1987)) expressed in appropriate host strains (2,5-DKG producers) such as *Erwinia sp.* These results have been achieved despite 2,5-DKG reductase A having a low specificity constant for 2,5-DKG. Since Corynebacterium does not naturally encounter 2,5-DKG, it is not surprising that this compound is a poor substrate for 2,5-DKG reductase A.

This low specificity constant for 2,5-DKG reductase A is in contrast to a second, homologous Corynebacterium 2,5-DKG reductase (2,5-DKG reductase B, also known as 2,5-DKG reductase I) that has a greater specificity constant for 2,5-DKG (Sonoyama and Kobayashi, J. Ferment. Technol. 65: 311–317 (1987)). In addition, both 2,5-DKG reductases are homologous to several known aldose and ketoreductases that have greater specificity constants towards their known substrates. Such findings indicate that the active site of 2,5-DKG reductase A is not optimally configured for the catalytic conversion of 2,5-DKG to 2-KLG. Therefore, it appears that in order to optimize 2,5-DKG reductase A specific activity in the single-fermentation process, amino acid substitutions by site-directed mutagenesis must be made to the enzyme's active site.

In addition to improving an enzyme's kinetic parameters, site-directed mutagenesis can increase structural stability by amino acid substitutions, deletions, or insertions. The following are examples of structurally stabilizing mutations. The introduction of new disulfide bonds to create covalent crosslinks between different parts of a protein has been used to improve the thermal stability of bacteriophage T4 lysozyme (Matsumura et al., Nature 342:291–293 (1989)), bacteriophage λ repressor (Sauer et al., Biochem. 25:5992–5998 (1986)), E. coli dihydrofolate reductase (Villafranca et al., Biochem. 26:2182–2189 (1987)), and subtilisin BPN' (Pantoliano et al., Biochem. 26:2077–2082

(1987)). There is a computer program (Pabo et al., Biochem. 25:5987–5991 (1986)) that permits efficient scanning of the crystallographically determined three-dimensional structure of a protein to suggest those sites where insertion of two cysteines might lead to disulfide bonds. Such bonds would not disrupt the larger-scale conformation, while stabilizing the local conformation.

Amino acid substitutions of alanine for glycine in the α-helix have been shown to increase the thermal stability of the bacteriophage λ repressor (Hecht et al., Proteins: Struct. Funct. Genet. 1:43–46 (1986)) and the neutral protease from *Bacillus stearothermophilus* (Imanaka et al., Nature 324:695–697 (1986)). An increase in the melting temperature, Tm, for bacteriophage T4 lysozyme was accomplished by the two amino acid substitutions of proline for alanine and alanine for glycine (Matthews et al., Proc. Nat. Acad. Sci. USA 84:6663–6667 (1987)). Replacement of amino acids in the hydrophobic core of a protein with aromatic residues such as tyrosine, especially at positions near pre-existing clusters of aromatic side chains, has been shown to promote thermal stability in kanamycin nucleotidyl transferase (Liao et al., Biochem. 83:576–580 (1986)) and bacteriophage λ repressor (Hecht et al., Biochem. 81:5685–5689 (1984)).

Transcriptional and translational control sequences in expression vectors are the key elements required for the high level production of proteins in bacteria. The *E. coli* Trp, bacteriophage λP$_L$, *E. coli* lac UV5, and the Trp-lacUV5 fusion (Tac) promoters are among the most frequently used prokaryotic promoters (de Boer et al., Proc. Nat. Acad. Sci. USA 80: 21–25 (1983); Sambrook et al., Molecular Cloning, Cold Spring Harbor Press (1989); Remaut et al., Gene 15:81–93 (1981)). There is no way to determine whether a particular protein will be highly expressed upon induction of transcription from these promoters. The translational efficiency of the message, mRNA stability, and the protein's intrinsic stability are the major factors in high-level expression. Therefore, whenever a protein undergoes mutagenesis it is always possible its expression level will be affected.

Site-directed mutagenesis, using synthetic DNA oligonucleotides having the desired sequence, permits substitution, deletion, or insertion of selected nucleotides within a DNA sequence encoding a protein of interest. Recombinant DNA procedures are used to introduce the desired mutation by substituting the synthetic sequence for the target sequence. Development of plasmids containing an origin of replication derived from a filamentous bacteriophage (Vieira and Messing, Methods in Enzymology 153: 3–11 (1987)) permits cloning of fragments into single stranded forms of plasmids capable of autonomous replication. Use of such plasmids eliminates the arduous task of subcloning DNA fragments from plasmids to filamentous bacteriophage vectors. Kits for carrying out site-directed mutagenesis are commercially available.

Mutants of 2,5-DKG reductase A having characteristics which vary from the native enzyme would be useful. In particular, mutants having improved catalytic activity, enhanced thermal stability, and increased expression levels would be useful to extend the commercial utility of the enzyme.

Unfortunately, unless proteins share regions of substantial sequence or structural homology, it is not possible to generalize among proteins to predict, based on a beneficial mutation of one protein, precisely where the sequence encoding another protein should be changed to improve the performance of that protein. Therefore, it is necessary to undertake an analysis of the precise structural and functional features of the particular protein to be altered. This determines which amino acids to alter to produce a desired result, such as increased catalytic activity, thermostability, or expression.

The present invention provides mutated forms of enzymatically active prokaryotic 2,5-DKG reductase A. Analysis of the structure of 2,5-DKG reductase A to select alterations encoding the enzyme to enhance stability, expression, and/or activity of resulting mutants was undertaken. Site-directed mutagenesis of the sequence encoding the enzyme was designed to produce the mutants.

SUMMARY OF THE INVENTION

The present invention provides mutants containing specific modifications of 2,5-DKG reductase A, and materials and methods useful in producing these proteins, as well as modified microorganisms and cell lines useful in their production. Other aspects of the invention include the expression constructs and products thereof for the modified 2,5-DKG reductases as well as cloning vectors containing the DNA encoding the modified 2,5-DKG reductases.

The DNA encoding the wild-type 2,5-DKG reductase A is modified using site-directed mutagenesis employing a single stranded form of plasmid which enables the generation of a change at a selected site within the coding region of the 2,5-DKG reductase A. By this method, a change is introduced into isolated DNA encoding 2,5-DKG reductase A which, upon expression of the DNA, results in substitution of at least one amino acid at a predetermined site in the 2,5-DKG reductase A. Also using this method, a change is introduced into isolated DNA encoding 2,5-DKG reductase A which, upon transcription of the DNA, results in substitution of at least one nucleotide at a predetermined site in the mRNA of the 2,5-DKG reductase A which allows increased expression.

The modified 2,5-DKG reductases and coding sequences of the invention may exhibit improved stability, expression, and/or catalytic activity, and may have varied Km and Vmax.

DETAILED DESCRIPTION OF THE INVENTION

Definitions

Figure 1:
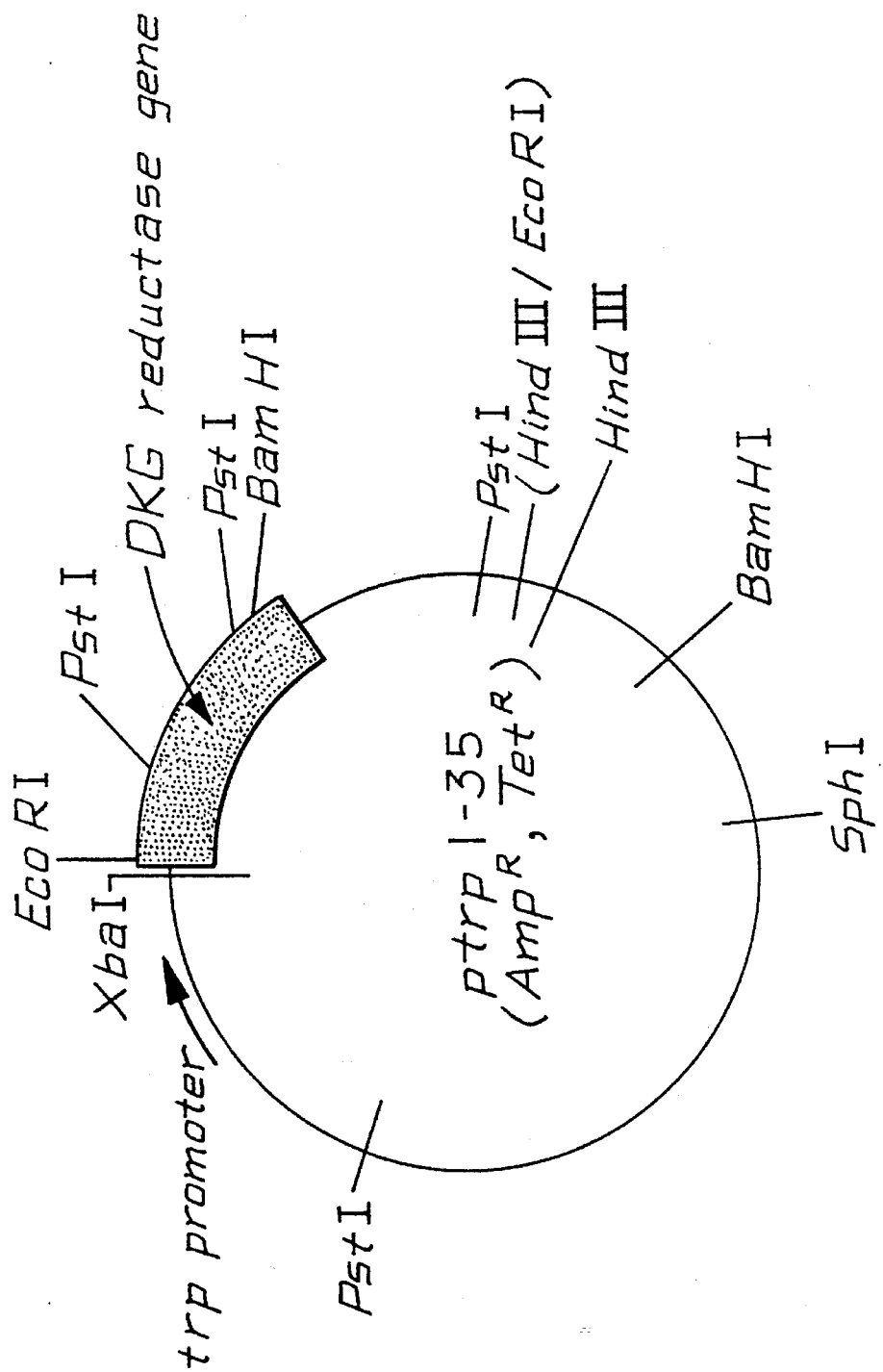
FIG. 1 shows an expression vector for the 2,5-DKG reductase A gene.

As used herein, "wild-type" 2,5-DKG reductase A refers to a protein which is capable of catalyzing the conversion of 2,5-DKG stereoselectively to 2-KLG. The wild-type enzyme is the enzyme prior to the modifications as described herein. The enzyme is obtained from the *Corynebacterium sp.* derived from ATCC strain No. 31090 as described in U.S. Pat. No. 5,008,193, incorporated herein by reference.

"Mutant" in relation to the "wild-type" 2,5-DKG reductase A, refers to a protein having a related amino acid sequence which has enzymatic activity substantially the same as the reference 2,5-DKG reductase A in that the enzyme converts 2,5-DKG to 2-KLG. However, it contains one or more amino acid substitutions, deletions, or insertions of amino acid residues. These residues have been selected by using certain approaches to predict those regions of the protein that are most likely to contain active site residues. One approach involves using secondary structural predictions to assign 2,5 DKG reductase A to an eight-stranded α/β barrel structure. A number of modifications are undertaken to modify the gene to encode mutants of the enzyme with improved characteristics compared to the wild-type enzyme, for converting 2,5-DKG stereoselectively into 2-KLG.

It is well understood in the art that many of the compounds discussed in the instant specification, such as proteins and the acidic derivatives of saccharides, may exist in a variety of ionization states depending upon their surrounding media, if in solution, or out of the solutions from which they are prepared if in solid form. The use of a term such as, for example, gluconic acid, to designate such molecules is intended to include all ionization states of the organic molecule referred to. Thus, for example, both "D-gluconic acid" and "D-gluconate" refer to the same organic moiety, and are not intended to specify particular ionization states. It is well known that D-gluconic acid can exist in unionized form, or may be available as, for example, the sodium, potassium, or other salt. The ionized or unionized form in which the compound is pertinent to the disclosure will either be apparent from the context to one skilled in the art or will be irrelevant. Thus, the 2,5-DKG reductase A protein itself and its various mutants may exist in a variety of ionization states depending on pH. All of these ionization states are encompassed by the terms "2,5-DKG reductase A" and "mutant form of 2,5-DKG reductase A."

"Expression vector" includes vectors which are capable of expressing DNA sequences contained therein where such sequences are operably linked to other sequences capable of effecting their expression. It is implied, although not explicitly stated, that expression vectors must be replicable in the host organisms either as episomes or as an integral part of a chromosomal DNA. Clearly, a lack of replication would render them effectively inoperable. In sum, "expression vector" is also given a functional definition. Generally, expression vectors of utility in DNA recombinant techniques are often in the form of "plasmids". Plasmids refer to either circular double stranded DNA molecules or circular single stranded DNA molecules, containing an origin of replication derived from a filamentous bacteriophage. These DNA molecules, in their vector form, are not linked to the chromosomes. Other effective vectors commonly used are phage and non-circular DNA. In the present specification, "plasmid" and "vector" are often used interchangeably. However, the invention is intended to include such other forms of expression vectors which serve equivalent functions and which are, or subsequently become, known.

"Recombinant host cells", "host cell", "cells", "cell cultures" and so forth are used interchangeably to designate individual cells, cell lines, cell cultures, and harvested cells which have been or are intended to be transformed with the recombinant vectors of the invention. The terms also include the progeny of the cells originally receiving the vector.

"Transformed" refers to any process for altering the DNA content of the host. This includes in vitro transformation procedures such as calcium phosphate or DEAE-dextran-mediated transfection, electroporation, nuclear injection, phage infection, or such other means for effecting controlled DNA uptake as are known in the art.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
|-----|---|---------------|-----|---|------------|
| Thr | T | threonine     | Leu | L | leucine    |
| Ser | S | serine        | Tyr | Y | tyrosine   |
| Glu | E | glutamic acid | Phe | F | phenylalanine |
| Pro | P | proline       | His | H | histidine  |
| Gly | G | glycine       | Lys | K | lysine     |
| Ala | A | alanine       | Arg | R | arginine   |
| Cys | C | cysteine      | Trp | W | tryptophan |
| Val | V | valine        | Gln | Q | glutamine  |
| Met | M | methionine    | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

TABLE 1

| Original Residue | Conservative Substitutions |
|------------------|----------------------------|
| Ala | ser |
| Arg | lys |
| Asn | gln; his |
| Asp | glu |
| Cys | ser; ala |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or stabilization are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteinyl or prolyl is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanyl, is substituted for (or by) one not having a side chain, e.g., glycyl.

General Methods

Most of the techniques which are used to transform cells, construct vectors, effect hybridization with a probe, carry out site-directed mutagenesis, and the like as well as the selection of mutants, are widely practiced in the art. Most practitioners are familiar with the standard resource materials which describe specific conditions and procedures (see for example, Sambrook et al., Molecular Cloning: A Laboratory Manual, Cold Spring Harbor Press (1989). However, for additional guidance the following paragraphs are presented.

Expression of 2,5-DKG Reductase A

The complete functional gene is ligated into a suitable expression vector containing a promoter and ribosome binding site operable in the host cell into which the coding sequence will be transformed. In the current state of the art, there are a number of promotion/control systems and suitable prokaryotic hosts available which are appropriate to the present invention. Similar hosts can be used both for cloning and for expression since prokaryotes are, in general, preferred for cloning of DNA sequences. The method of 2-KLG production is most conveniently associated with such microbial systems. *E. coli* K12 strain 294 (ATCC No. 31446) is particularly useful as a cloning host. Other microbial strains which may be used include *E. coli* strains such as *E. coli* B, *E. coli* X1776 (ATCC No. 31537) and *E. coli* DH-1 (ATCC No. 33489). For expression, the aforementioned strains, as well as *E. coli* W3110 (F-, λ-, prototrophic ATCC No. 27325), bacilli such as *Bacillus subtilus*, and other enterobacteriaceae such as *Salmonella typhimurium* or *Serratia marcesans*, and various *Pseudomonas* species may be used. A particularly preferred group of hosts includes those cultures which are capable of converting glucose or other commonly available metabolites to 2,5-DKG. Examples of such hosts are generally found among the genera Acetobacter, Gluconobacter, Acetomonas, and Erwinia. The taxonomy and nomenclature of these genera are such that the same or similar strains are sometimes given different names. For example, *Acetobacter cerinus* used in the example below is also referred to as *Gluconobacter cerinus*. Examples of particular hosts include but are not limited to, *Erwinia herbicola* ATCC No. 21998 (also considered an *Acetomonas albosesamae* in U.S Pat. No. 3,998,697); Acetobacter (Gluconobacter) oxydans subspecies melanozenes, IFO 3292, 3293 ATCC No. 9937; Acetobacter (Gluconobacter) cerinus IFO 3263 IFO 3266; *Gluconobacter rubiginous*, IFO 3244; *Acetobacter fragum* ATCC No. 21409; *Acetobacter (Acetomonas) suboxydans* subspecies industrious ATCC No. 23776.

In general, plasmid expression or cloning vectors or conjugative plasmids containing replication and control sequences which are derived from species compatible with the host cell are used in connection with these hosts. The vector ordinarily carries a replication origin as well as marker genes which are capable of providing phenotypic selection in transformed cells. For example *E. coli* is typically transformed using pBR322, a plasmid derived from an *E. coli* strain (Bolivar et al., Gene 2:95–113 (1977)). pBR322 contains genes for ampicillin and tetracycline resistance and thus provides easy means for identifying transformed cells. For use in expression, the pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al., Nature 275: 617–624 (1978); Itakura et al., Science 198:1056–1063 (1977); Goeddel et al., Nature 281:544–548 (1979)) and a tryptophan (trp) promoter system (Goeddel et al., Nucleic Acids Res. 8:4057–4074 (1980); EPO Application No. 0036776). While these are the most commonly used, other microbial promoters have been discovered and utilized. Details concerning their nucleotide sequences have been published, enabling a skilled worker to ligate them functionally in operable relationship to genes in transformation vectors. (Siebenlist et al., Cell 20:269–281 (1980)).

By suitable cleavage and ligation, DNA sequences encoding 2,5-DKG reductase A can be included in the aforementioned vectors prepared as outlined above. Any unnecessary or inhibitory sequences may be deleted and the prokaryotic enzyme may then be purified; or the intact or broken cells used directly as catalysts. Alternatively, the host may be chosen so that once transformed it is capable of effecting the entire conversion of glucose or other suitable metabolite to the desired 2-KLG product.

Both the wild-type plasmid DNA and mutant plasmid DNA for 2,5-DKG reductase A is transfected into a host for enzyme expression. The recombinant host cells are cultured under conditions favoring enzyme expression. Usually selection pressure is supplied by the presence of an antibiotic. The resistance to the antibiotic is encoded by the vector. Culture under these conditions results in enzyme yields greater than the wild-type enzyme synthesis of the parent organism. This is the case, even if it is the parent organism that is transformed.

Vector Construction For Mutagenesis

Figure 2:
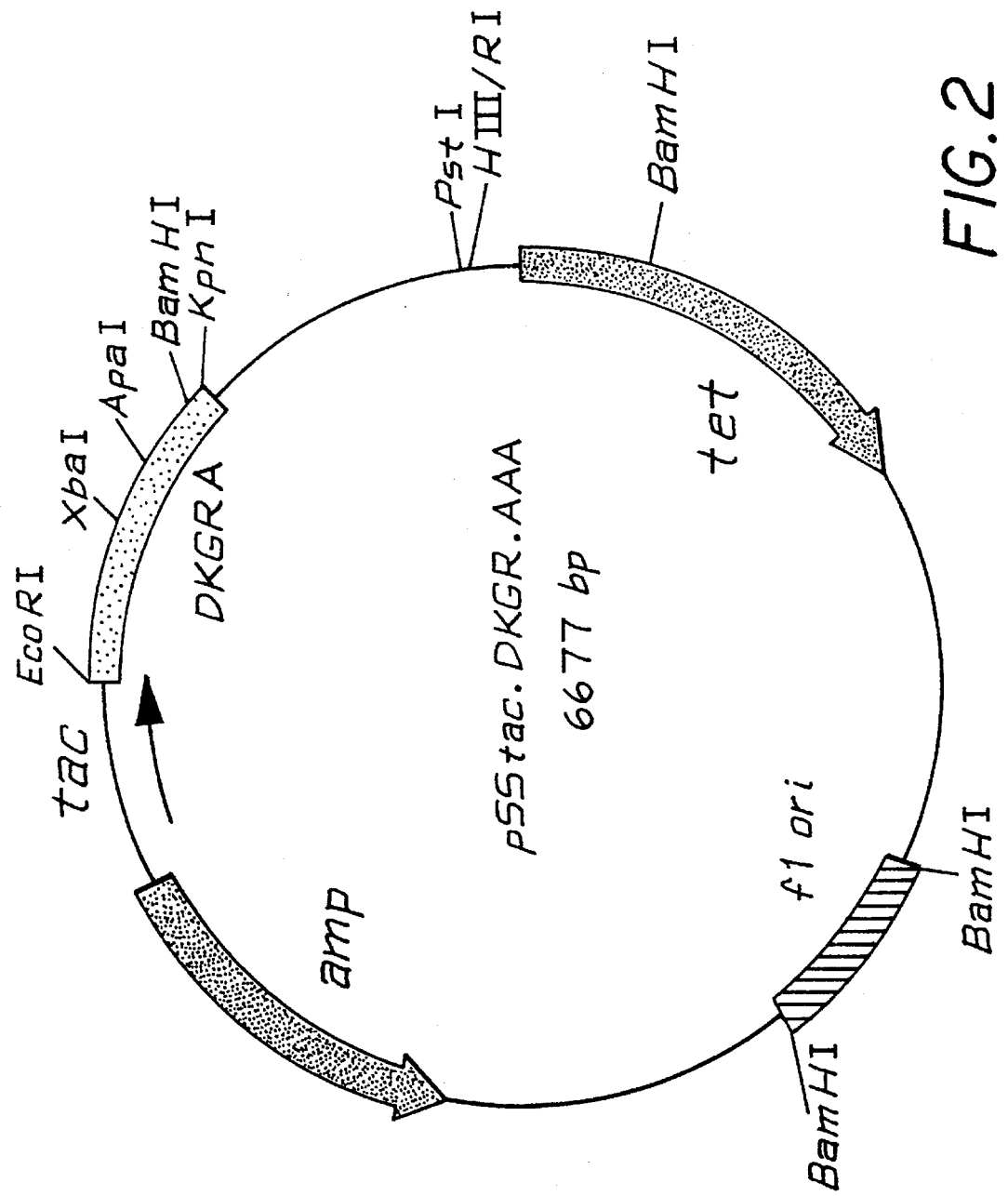
FIG. 2 shows an expression vector for producing mutant forms of 2,5-DKG reductase A.

Anderson et al have described the construction of plasmid ptrpl-35 in U.S. Pat. No. 5,008,193, incorporated herein by reference, that contains the cloned DKG reductase A gene under the control of the *E. coli* trp promoter (FIG. 1). A derivative of this plasmid is constructed, with a few minor modifications to facilitate construction and characterization of mutant forms of 2,5-DKG reductase A. These modifications are described below. The final plasmid construct is called pSStac.DKGR.AAA and is shown in FIG. 2.

A) The structural gene for 2,5-DKG reductase A is mutated to include three new restriction enzyme sites to facilitate further mutagenesis studies. These three sites are "silent," i.e., the amino acid sequence of the resulting DKGR A protein remains unchanged.

B) The promoter in pSStac.DKGR.AAA is the tac II promoter described by de Boer et al (Proc. Nat. Acad. Sci. USA 80:21–25 (1983)) instead of the trp promoter found in ptrpl-35. This is a modified version of the trp promoter containing the binding site for lac repressor, allowing the expression of the gene to be regulated in cells expressing the lac repressor.

C) The plasmid is further modified to include the origin of replication from the single stranded filamentous phage f1. The use of this DNA sequence in plasmids is well known in the art to produce a single stranded form of the plasmid for sequencing and mutagenesis.

Site-Directed Mutagenesis

After the desired modifications are selected, the DNA sequence encoding the 2,5-DKG reductase A is subjected to site-directed mutagenesis to substitute nucleotides encoding selected amino acids at the predetermined positions within the sequence.

The preferred procedure for site-directed mutagenesis is performed by cloning the DNA sequence encoding the wild-type enzyme into a recombinant plasmid containing an origin of replication derived from a single-stranded bacteriophage. Then an appropriate primer is used to convert a residue at an identified position for example, to a conservative amino acid replacement. A synthetic oligonucleotide primer complementary to the desired sequence, except in areas of limited mismatching, is used as a primer in the synthesis of a strand complementary to the single-stranded wild-type 2,5-DKG reductase A sequence in the plasmid vector. The resulting double-stranded DNA is transformed into a host bacterium. Cultures of the transformed bacteria are plated on agar plates, permitting colony formation from single cells which harbor the plasmid. Theoretically, 50% of the colonies will consist of plasmid containing the mutant form; 50% will have the original sequence. The colonies are hybridized with radiolabelled synthetic primer under stringency conditions which permit hybridization only with the mutant plasmid which will form a perfect match with the probe. Hybridizing colonies are then picked and cultured, and the mutant plasmid DNA is recovered.

Selection Of Sites For Mutagenesis Of Mutants For The Wild-Type

2,5-DKG Reductase A Gene

Crucial to selection of sites for mutagenesis is prediction of a secondary and tertiary structure of the wild-type enzyme. The secondary structural predictions are carried out in the following manner. First, the sequences of 2,5 DKG reductases A and B, and five other homologous enzymes (prostaglandin F synthase, bovine lens and rat lens aldose reductase, human liver aldehyde reductase, and p-crystallin from frog eye lens) are aligned to reveal a number of conserved residues. Second, the sequences are subjected to a number of structure prediction algorithms (Chou and Fasman, Adv. Enzymol. 47:45–148 (1978); Garnier et al., J. Mol. Biol. 120:97–120 (1978); Wilmot and Thornton, J. Mol. Biol. 203: 221–232 (1988); Karplus and Schulz, Naturwissenschaften 72: 212–214 (1985); Eisenberg et al., Proc. Nat. Acad. Sci. USA 81:140–144 (1984); Rose and Roy, Proc. Nat. Acad. Sci. USA 77:4643–4647 (1980)) well known in the art. These predictions are collated and compared to derive a rough model of the enzyme's secondary structure as an eight-stranded α/β barrel. This secondary structure prediction is consistent with the recently solved secondary structures of homologous enzymes having the fold of an eight-stranded α/β barrel (Rondeau et al., Nature 355:469–472 (1992); Wilson et al., Science 257:81–84 (1992)).

The barrel structure is composed of two components. The first component is a core of eight twisted parallel beta strands arranged close together, like staves, into a barrel. Surrounding this barrel structure is a second component of eight alpha helices that are joined to the beta strands through loops of various lengths. This eight-stranded α/β barrel structure is called the triosephosphate isomerase (TIM) barrel from the enzyme for which this structure was first observed. The folding pattern of the α/β barrel is found in 17 enzymes whose crystal structures are known. In fact, approximately 10% of known enzyme structures are α/β barrels (Farber and Petsko, TIBS: 228–234 (June 1990)).

The 17 known α/β barrel enzymes have a common α/β barrel core; substrate and cofactor specificity comes from the variable loops joining the beta strands and alpha helices.

Figure 3:
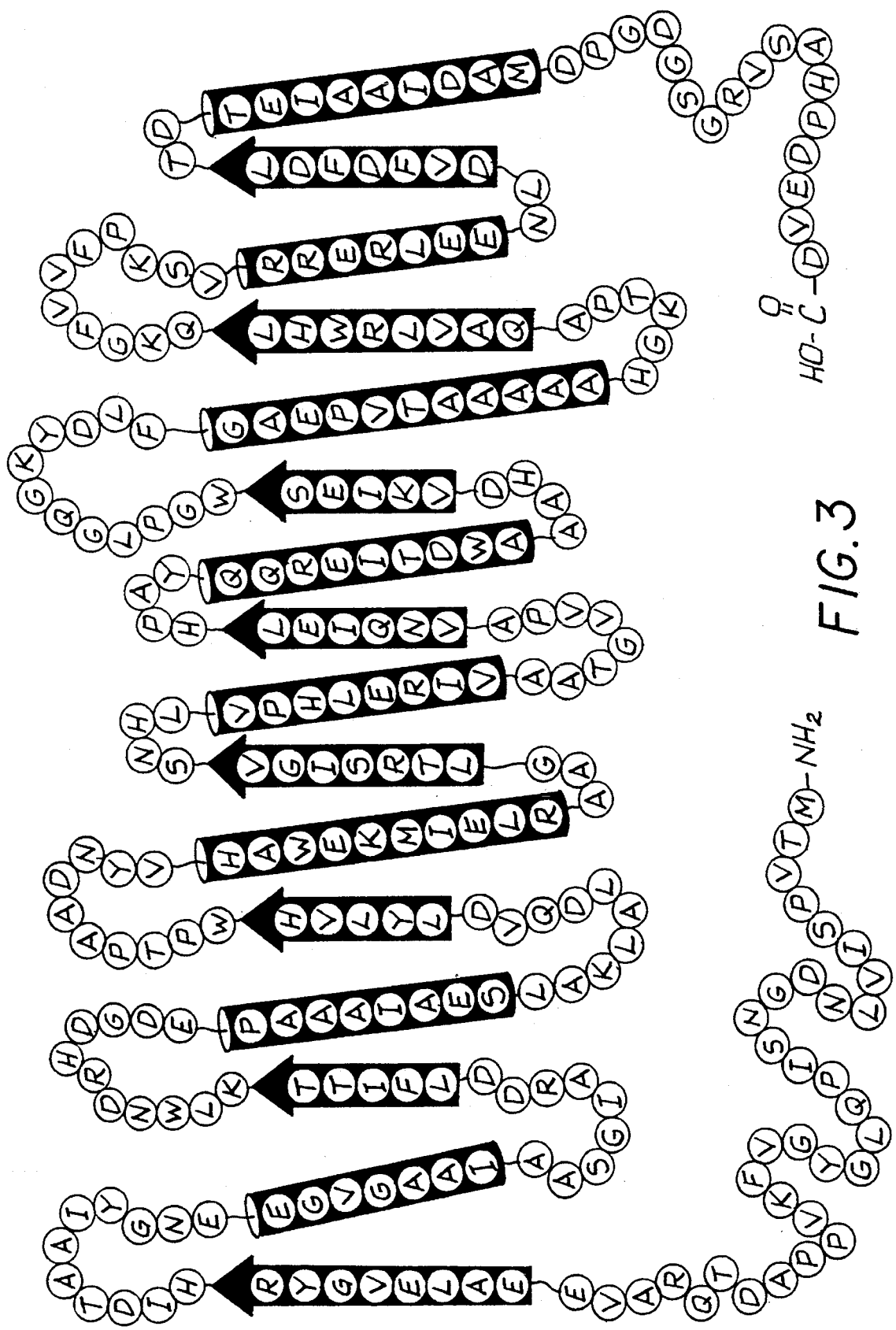
FIG. 3 (SEQ. ID No. 1) shows schematically a proposed model for 2,5-DKG reductase A.

The proposed secondary structure model for 2,5-DKG reductase A, based on a consensus of secondary structure predictions on members of the aldose reductase family (see above), is shown schematically in FIG. 3 (SEQ. ID NO: 1), where beta strands are represented by arrows and the alpha helices are shown as cylinders. Regions of polypeptide chain connecting the predicted elements of secondary structure are indicated as of undefined structure. There are N and C terminal extensions of 34 and 17 amino acids, respectively. Such extensions in the TIM-barrel enzymes often form alpha helices that fold back over the top or bottom of the barrel. Some subset of the eight loops at the C terminus of the beta sheet (towards the top of FIG. 3 (SEQ. ID NO: 1), as well as the C-terminal "tail" (positions 262 to 278) are thought to comprise the active site of the enzyme, as in the other TIM-barrel enzymes. Although only a rough model, this structure greatly facilitates rational engineering of the enzyme, by allowing the focus towards those residues found in proposed active site loops. It will be apparent that additional residues near to those in the proposed loops and "tail" may also comprise part of the active site.

Such information as to which amino acids comprise the active site of an enzyme can be gained from knowledge of the actual three dimensional shape of the enzyme in question, as obtained from x-ray crystallographic or NMR studies. In the case of 2,5-DKG reductase, no such structural information yet exists in the published literature. Therefore, an alternate strategy in such a case would be using the model for 2,5-DKG reductase A as an α/β barrel discussed above, to limit the possible single amino acid replacements to those residues found in proposed active site loops.

By such an approach, the three surface loops that are the substrate binding site of 2,5-DKG reductase A are identified. These loops are at positions 165–168, 187–198, and 224–234. A set of twelve 2,5-DKG reductase A mutants is made in these loops. This set comprises nearly all possible point substitutions from the 2,5-DKG reductase B sequence. Many of these mutants, show major reductions in activity for converting 2,5-DKG to 2-KLG, even when only minor or conservative changes are made in the amino acids. One of the mutants, with a substitution of arginine for glutamine at position 192 in the 2,5-DKG reductase A sequence, has an improved ability to convert 2,5-DKG into 2-KLG. The construction of this mutant, named "Q192R" is described in Example 2.

The twelve mutants are expressed in *Acetobacter cerinus* and assayed for conversion of 2,5-DKG to 2-KLG at the crude lysate stage. Table 2 below includes a comparison of the activities of the twelve 2,5-DKG reductase A mutants against the wild-type 2,5-DKG reductase A and 2,5-DKG reductase B. Assays in Table 2 are carried out as described in Table 3 below. The increased activity of Q192R at the crude lysate stage, although somewhat obscured by the high levels of background reductase activity as seen in the pBR322 control lysates, is nonetheless significant and reproducible. The data for the pBR322, wild-type enzyme, and Q192R mutant in Table 2 are the average of three separate lysate assays. By assuming a simple additive contribution of the background reductase activity in these lysates, these data show that the Q192R mutant is twice as active as the wild-type enzyme against 2,5-DKG. Characterization of the kinetic constants of purified Q192R yields an improved Km and Vmax for this enzyme relative to wild type 2,5-DKG reductase A. See Example 5. Thus, Q192R shows improvement over the natural enzyme both in specificity (Km) and in turnover rate (Vmax).

In a manner similar to that described above, the C-terminal "tail" is also identified as part of the active site. A truncation mutant is designed that results in polypeptide termination before the last eight amino acid residues of 2,5-DKG reductase A. This mutant is found to be well expressed, and the cofactor binding site is preserved, but, as shown in Table 2 below, it is absolutely inactive using 2,5-DKG as a substrate. By this criteria the C-terminal "tail" is inferred to comprise part of the binding pocket for 2,5-DKG.

TABLE 2

| Lysate Identity | | % Wild-type on 2,5-DKG |
|---|---|---|
| pBR322 (control) | | 0% |
| 2,5-DKG Reductase A | | 100% |
| 2,5-DKG Reductase B | | >>>600% |
| (alanine for glycine at position 191) | G191A mutant | 1% |
| (arginine for glutamine at position 192) | Q192R mutant | 200% |
| (glycine deleted at position 193) | G193 deleted mutant | 0% |
| (arginine for lysine at position 194) | K194R mutant | 8% |
| (serine for tyrosine at position 195) | Y195S mutant | 6% |
| (tyrosine for alanine at position 167) | A167Y mutant | 0% |
| (phenylalanine for tyrosine at position 168) | Y168F mutant | 2% |
| (proline for glutamine at position 169) | Q169P mutant | 15% |
| (leucine for lysine at position 225) | K225L mutant | 5% |
| (serine for phenylalanine at position 227) | F227S mutant | 12% |
| (threonine for valine at position 228) | V228T mutant | 23% |
| (proline for valine at position 229) | V229P mutant | 22% |
| (stop codon at position 271) | truncation mutant (missing last eight amino acids) | 0% |

Without using the α/β barrel model as guidance, a random search of all possible single amino acid replacements is necessary. This requires the construction and assay of 170 such enzymes, reflecting the differences between the enzymes for possible recruitment of 2,5-DKG reductase B-like activity onto the 2,5-DKG reductase A framework.

Glycine residues in alpha helices that can accept the increased bulk of the substituted methyl group, are substituted with alanine residues to introduce stabilization. Introduction of aromatic amino acid residues such as tyrosine, phenylalanine, and tryptophan near aromatic clusters within the enzyme are also within the scope of the invention. These additional aromatic residues stabilize the enzyme at sites where the introduction of such aromatic groups will not distort the overall conformation.

Mutations at particular sites in a protein can lead to enhanced expression of that protein in bacteria. At the present time there is no way to predict which mutations lead to enhanced expression. However, it is known that the factors of translational efficiency, mRNA stability, and increased protein stability play a key role in high-level expression.

Many of the other possible point mutants are generated in clusters of one to four closely spaced amino acid substitutions. Of the mutants which are stably folded, only those falling in the 165–168 loop, 187–198 loop, 224–234 loop, and C-terminal "tail" (262–278) exhibit activity significantly different from the wild type enzyme. This is additional confirmation that these loop and tail regions comprise the enzyme active site.

Any number of mutations proposed herein may be combined in a single mutant. Obviously, a particular substitution at one location rules out replacement with another amino acid at that same location in that particular mutant.

The following examples are presented to illustrate the present invention and to assist one of ordinary skill in making and using the same. The examples are not intended in any way to otherwise limit the scope of the invention.

EXAMPLE 1

Construction Of Plasmid pSStac.DKGR.AAA For Mutagenesis

An aliquot of plasmid ptrpl-35 was digested with EcoRI and HindIII restriction enzymes and the resulting 1690 base pair fragment purified by agarose gel electrophoresis. This fragment was then ligated into EcoRI and HindIII digested vector M13 mp19. The resulting recombinant phage (called M13 mp19. DKGRA) was used to isolate a single stranded template form of the phage for subsequent mutagenesis. The template was mutagenized with three oligonucleotides to introduce three new restriction enzyme cleavage sites to the 2,5-DKG reductase A gene. These sites are all 'silent' in that although they introduce a new restriction cleavage site to the DNA sequence, the amino acid sequence of the protein coded for remains unchanged, due to degeneracy in the genetic code. The three mutagenic oligonucleotides and the changes introduced are as follows: 1) oligonucleotide XbaA has sequence 5'CGCGAAGCTGGCTCTAGATCAGGTC-GAC 3' (SEQ ID NO: 2) and introduces a new XbaI site at amino acid position 98; 2) oligonucleotide ApaA has sequence 5' ATCGTGGGGGCCCCTCGGTCAGGGC 3' and introduces a new ApaI site at amino acid position 188; and 3) oligonucleotide KpnA has sequence 5' GAGGTC-GACTGAGGTACCCGAACACCCG 3' (SEQ ID NO: 4) and introduces a new KpnI site immediately following the stop codon (TGA) after the final amino acid. The mutagenesis reaction and conditions were essentially the same as described in Example 2 for the construction of mutant Q192R. After the mutagenesis reaction, positives plaques were identified by hybridization to the mutagenic oligonucleotide under stringent conditions, and the entire coding region of the 2,5-DKG reductase A fragment was sequenced to confirm the mutations.

The plasmid pSStac.DKGR.AAA was constructed as a three way ligation of the following fragments: 1) EcoRI to HindIII from the mutagenized phage M13 mp19.DKGRA as described above, this contains the coding gene for 2,5-DKG reductase A; 2) the PstI to EcoRI fragment (850 base pairs) from plasmid ptac6 (ptac6 is equivalent to plasmid ptrpl-35 but contains the tac promoter as described in de Boer et al. (Proc. Nat. Acad. Sci. USA 80:21–25 (1983)) instead of the trp promoter found in ptrpl-35), and 3) the ~4,000 base pair vector fragment from HindIII to PstI of plasmid p690. The p690 plasmid is a derivative of plasmid pBR322 with the RsaI/DraI restriction fragment from the genome of bacteriophage f1 (nucleotides 5489–5946), containing the single-stranded DNA origin of replication, inserted into the PvuII site.

The three fragments described above were isolated by agarose gel electrophoresis, purified, and ligated in approximately equimolar ratios, and used to transform competent *E. coli* cells. The resulting colonies were analyzed by restriction mapping to identify the correct construct, called pSStac.DKGR.AAA (FIG. 2).

EXAMPLE 2

Site-Directed Mutagenesis Of The 2,5-DKG Reductase A Gene

A. Preparation of Template DNA For Mutagenesis

*E. coli* cells (strain XL1-Blue, Stratagene Corporation) bearing plasmid pSStac.DKGR.AAA were grown in LB media (Sambrook et al., Molecular Cloning: A Laboratory Manual, Cold Spring Harbor Press, A.1 (1989)) to early log phase, and infected with helper phage VCS-M13 (Stratagene). Infection with helper phage provides needed factors for the packing and secretion of the single-stranded form of plasmid pSStac.DKGR.AAA. The infected cells were grown overnight with shaking at 37° C., and the next day the cells were removed by centrifugation at 10,000 rpm for 10 minutes in a Sorvall SM24 rotor. The supernatant containing the packaged plasmid was retained and the cell pellet discarded. The packaged plasmid was precipitated by the addition of ¼ volume of 2.5 M NaCl, 20% PEG (polyethylene glycol). After addition the mixture was stored at room temperature for 20 minutes, and then the precipitate was recovered by centrifugation.

The precipitate was dissolved in 0.4 ml of TE buffer (10 mM tris, pH 7.5, 1 mM EDTA) and further purified by several sequential extractions with an equal volume of 50:50 chloroform:phenol. After each extraction the aqueous (upper) phase was retained. The pure plasmid was precipitated with 2 volumes of ice-cold ethanol. The precipitate was recovered by centrifugation and dissolved in TE buffer. The concentration of the plasmid was estimated by measuring the optical absorbance at 260 nm using the conversion of 1 $OD_{260}$=40 µg of single stranded DNA per milliliter. The concentration of the plasmid was adjusted to 1 µg per ml with TE.

B. Phosphorylation Of Oligonucleotide Primer

A synthetic oligonucleotide with the sequence

5' GCCCCTCGGTCGCGGCAAGTACG 3' (SEQ ID NO: 5) was synthesized and phosphorylated as follows: the oligonucleotide was diluted to a concentration of 5.0 $OD_{260}$ units per ml. Then 2.5 µl of oligonucleotide was combined with 3 µl 10x kinase buffer (1 M tris pH 8.0, 100 mM $MgCl_2$, 70 mM dithiothreitol, 10 mM ATP), 25 µl water, and 2 units of T4 polynucleotide kinase (New England Biolabs). The mixture was incubated at 37° C. for 15 minutes, then the kinase enzyme was inactivated by heating to 70° C. for 10 minutes.

C. Mutagenesis Reaction

Six µl of kinased primer were combined with 1 µg of template DNA and 2.5 µl of 10x RB buffer (70 mM tris, pH 7.5, 50 mM mercaptoethanol, 550 mM NaCl, and 1 mM EDTA) in a total volume of 10.5 µl. The primer was annealed to the template by heating the mixture to 65° C. for five minutes, then slowly cooling to room temperature over a 30 minute period.

To the annealing mixture was added 1.5 µl of 10x RB buffer, 1 µl of 10 mM ATP, 1 µl of 10 mM DTT (dithiothreitol), and 1 µl T4 DNA ligase (New England Biolabs). After 10 minutes, 1 µl of 1 M $MgCl_2$, 1 µl of 5mM dNTP's (an equimolar mixture of dATP, dCTP, dGTP, and dTTP) and 0.5 µl of Klenow (large fragment of DNA polymerase I, New England Biolabs) were added, and the mixture incubated at 15° C. overnight.

The following day, frozen competent *E. coli* MutL cells were transformed with an aliquot of the reaction mixture, and plated onto agar plates containing antibiotic selection (12.5 µg/ml tetracycline, 50 µg/ml ampicillin). Colonies bearing mutant plasmids were initially identified by hybridization to the original mutagenic oligonucleotide under stringent conditions (Wood et al, Proc. Nat. Acad. Sci. USA 82:1585–1588 (1988)). Mutant plasmids were then prepared in a single-stranded form as in Section A and confirmed by direct DNA sequencing of the plasmid (United States Biochemical Corporation, Sequenase sequencing kit). The resulting mutant Q192R 2,5-DKG reductase A, as shown in Example 5, had improved catalytic activity in comparison to the wild-type 2,5-DKG reductase A.

EXAMPLE 3

Expression Of Wild-Type 2,5-DKG Reductase A In *Acetobacter Cerinus*

Plasmid DNA was introduced into *Acetobacter cerinus* (ATCC No. 39140) by electroporation, as described (Wirth et al, Mol. Gen. Genet. 216 (1):175–177 (March 1989)) using a Genepulser apparatus (Biorad Corporation). Cells were grown to mid-log phase ($OD_{550}$ ~0.2–0.8) in 100 ml LB medium and recovered by centrifugation at 5,000 rpm in a Sorvall SS-34 rotor for 5 minutes at 4° C. The cells were resuspended in one half volume of ice-cold electroporation buffer (300 mM sucrose, 7 mM sodium phosphate buffer, pH 7.0, and 1 mM $MgCl_2$), again pelleted by centrifugation, and finally resuspended in 1/20th volume of electroporation buffer, and stored on ice until use. Plasmid DNA (0.1 to 1.0 µg) was added to a 0.4 cm electroporation cuvette (Biorad Corporation) which contained 0.8 ml of the prepared Acetobacter cells. The cells and DNA were mixed in the cuvette and cooled on ice for 10 minutes prior to electroporation. The cells and DNA were given a single pulse at 2500 mV using a 25 uF capacitor setting, and immediately diluted to 3.0 ml with fresh LB media. The diluted cells were then allowed to recover with shaking at 30° C. for 2 hours. Aliquots (10–100 µl ) of the transformed cells were plated on selective media (LB agar plates containing 50 µg/ml ampicillin and 12.5 µg/ml tetracycline) and the plates were grown overnight at 30° C.

EXAMPLE 4

Purification Of The Mutant Q192R And The Wild-Type 2,5-DKG

Reductase A

Single colonies from transformed *Acetobacter cerinus* cells were grown in 200 mls of 2 X YT media (Sambrook et al., Molecular cloning: A Laboratory Manual, Cold Spring Harbor Press, A.3 (1989)) containing antibiotics (12.5 µg/ml tetracycline and 50 µg/ml ampicillin) at 30° C. overnight. The cells were recovered by centrifugation (15 minutes at 8000 rpm in a Sorvall GS3 rotor) and stored frozen. The cells were then thawed in ⅕ volume of lysis buffer (50 mM tris, pH 8.0, 50 mMEDTA, 0.1% Tween, 2 mg/ml lysozyme) and lysed for two hours on ice. The lysed cells were again centrifuged as before, and the supernatant containing the crude cell extract retained.

The 2,5-DKG reductase A protein was purified from the crude cell extract by chromatography on DEAE cellulose. DEAE cellulose (Whatman DE-52 brand) was pre-equilibrated with 25 mM tris, pH 7.0. A total of 5.0 ml of the gel was poured into a disposable plastic chromatography column, to which was applied the crude cell extract. After all of the extract had been bound to the column, the column was washed with two column volumes of 25 mM tris pH 7.0, then one volume of 25 mM tris pH 7.0 containing 0.3 M NaCl, and finally the 2,5-DKG reductase A protein was eluted with 25 mM tris pH 7.0 containing 0.6 M NaCl. The preparations were assayed for protein concentration by the bicinchoninic acid method (Methods in Enzymology 182:60–62 (1990)) and checked for purity by SDS polyacrylamide gel electrophoresis.

EXAMPLE 5

Kinetic Characterization Of The Wild-Type And The Mutant

Q192R 2,5-DKG Reductase A

The preparations of wild-type and mutant Q192R 2,5-DKG reductase A enzymes were characterized kinetically as to their ability to reduce the substrate 2,5-DKG to 2-KLG. Assays were done in 1 ml total volume of 50 mM tris, pH 7.0, containing 0.2 mM NADPH, a constant amount of enzyme (15–20 mg) and amounts of substrate varying from 2 to 14 mM. The assays were done at 25° C., and the rate of substrate reduction was measured spectrophotometrically by measuring the loss of absorbance at 340 nm wavelength (which is indicative of the oxidation of the cofactor NADPH to NADP+).

The data were analyzed according to the well-known Michaelis equation to determine the kinetic parameters Vmax and Km using the Enzfit software package (Biosoft, Cambridge, UK) on a Epson desktop computer. The wild-type 2,5-DKG reductase A had a Vmax for the 2,5-DKG substrate of 7.8 µmoles per minute per milligram of protein, while the Q192R mutant had a Vmax of 14.0, a 1.8 fold improvement. The Km or Michaelis constant of the wild-type enzyme was 28 mM, while the Km of the Q192R mutant was 21 mM for this substrate. This led to a specificity constant (kcat/Km) of 140 $M^{-1} s^{-1}$ for the wild-type enzyme and a specificity constant of 335 $M^{-1} s^{-1}$ for the Q192R mutant, a 2.4 fold improvement.

EXAMPLE 6

A Mutant of 2,5-DKG Reductase A With Increased In-Vivo Expression

A mutant form of 2,5-DKG reductase A was discovered which, although having activity equivalent to the wild-type enzyme, had increased amounts of the protein accumulating in the Acetobacter expression host. This mutant, named "HS1", contains three amino acid changes: asparagine replaces threonine at position two, threonine replaces serine at position five, and serine replaces valine at position seven. The synthesis of this mutant was directed by a 37 base oligonucleotide with the sequence 5' AATTCTATGAACGT-TCCCACCATCAGCCTCAACGAC 3'(SEQ ID NO: 6). The steps in the mutagenesis reaction were essentially the same as outlined for construction of the Q192R mutant.

Table 3 below shows results of assays of crude cell lysates of Acetobacter cerinus bearing either: plasmid pBR322, a control plasmid that contains no 2,5-DKG reductase A sequence, pSStac.DKGR.AAA, the plasmid expressing the wild-type gene, or pSStac.DKGR.AAA.HS1, which contains the HS1 mutations. Crude cell extracts were prepared as described in the section on purification of 2,5-DKG reductase A and Q192R mutant protein. Results are shown for triplicate cell cultures.

TABLE 3

|   | assay values* | average | % wild-type |
|---|---|---|---|
| pBR322 | −0.031, −0.030, −0.041 | −0.034 | 0% |
| pSStac.DKGR.AAA | −0.158, −0.192, −0.186 | −0.178 | 100% |
| pSStac.DKGR.AAA.HS1 | −0.207, −0,214, −0.217 | −0.213 | 124% |

*values are the changes in absorbance at 340 nm per minute per 50 µl of crude cell extract, at a substrate concentration of 10 mM 2,5-DKG and 0.2 mM NADPH in 50 mM tris, pH 7.0, 25° C.

In these assays of crude cell lysates, it is necessary to account for background reductase from the Acetobacter cerinus cells themselves. This amount of activity is represented in the pBR322 cultures and is subtracted from the other values in order to calculate a "% wild-type activity."

Assays were done as before, in 1.0 ml total volume of 50 mM tris, pH 7.0, containing 0.2 mM NADPH, a single fixed amount of 2,5-DKG (10 mM), and 50 µl of crude cell lysate.

Cell cultures bearing pSStac.DKGR.AAA.HS1 consistently show a 20–30% increase in expression levels over cell cultures containing the wild-type plasmid pSStac.D-KGR.AAA. This increase in expression may be due to changes in mRNA stability, level of translation of the message, protein stability, or some combination of these effects.

EXAMPLE 7

A Mutant of 2,5-DKG Reductase A with Increased Temperature Stability

A mutant form of 2,5-DKG reductase A is discovered which has increased temperature stability in the Acetobacter expression host. This mutant contains two amino acid changes: alanine replaces glycine at position 55, and alanine replaces glycine at position 57. The synthesis of this mutant is directed by a base oligonucleotide with the sequence 5' GAAACGAAGAAGCGGTCGCGGCCGCGATCGCG 3'(SEQ ID NO: 7). The steps in the mutagenesis reaction are essentially the same as outlined for the construction of the Q192R mutant.

EXAMPLE 8

2,5-DKG Reductase A Mutants With Reduced Activity

Mutant forms of 2,5-DKG reductase A were discovered which showed major reductions in activity for converting 2,5-DKG to 2-KLG. The steps in the mutagenesis reactions were essentially the same as outlined for construction of the Q192R mutant. The following base oligonucleotides directed the synthesis of such mutants showing reduced activity in the Acetobacter expression host: with a substitution of alanine for glycine at position 191 to construct the G191A mutant, 5' GGGGCCGCTCGCCCAGGGCAAGT 3' (SEQ ID NO: 8); with a deletion of glycine at position 193 to construct the G193 deleted mutant, 5' CCGCTCGGTCA-GAAGTACGACCT 3' (SEQ ID NO: 9); with a substitution of arginine for lysine at position 194 to construct the K194R mutant, 5' CGGTCAGGGCCGCTACGACCTCT 3' (SEQ ID NO: 10); with a substitution of serine for tyrosine at position 195 to construct the Y195S mutant, 5' TCAGGGCAAGTCGGACCTCTTCG 3' (SEQ ID NO: 11); with a substitution of tyrosine for alanine at position 167 to construct the A167Y mutant, 5' GCTGCACCCCTACTAC-CAGCAGC 3' (SEQ ID NO: 12); with a substitution of phenylalanine for tyrosine at position 168 to construct the Y168F mutant, 5' GCACCCCGCCTTCCAGCAGCGCG 3' (SEQ ID NO: 13); with a substitution of proline for glutamine at position 169 to construct the Q169P mutant, 5' CCCCGCCTACCCGCAGCGCGAGA 3' (SEQ ID NO: 14); with a substitution of leucine for lysine at position 225 to construct the K225L mutant, 5' GCACCTGCAGCTCG-GTTTCGTGG 3' (SEQ ID NO: 15); with a substitution of serine for phenylalanine at position 227 to construct the F227S mutant, 5' GCAGAAGGGTTCGGTGGTCTTCC 3' (SEQ ID NO: 16); with a substitution of threonine for valine at position 228 to construct the V228T mutant, 5' GAAGGGTTTCACCGTCTTCCCGA 3' (SEQ ID NO: 17); with a substitution of proline for valine at position 229 to construct the V229P mutant, 5' GGGTTTCGTGCCCTTC-CCGAAGT 3' (SEQ ID NO: 18); and with a stop codon at position 271 to construct the truncation mutant, 5' GGGTCGCGTGTGAGCACACCCCG 3' (SEQ ID NO: 19).

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

---

What is claimed is:

1. A mutant form of a 2,5 diketo-gluconic acid reductase A, 2,5-DKG reductase A, enzyme having an ability to convert 2,5-DKG into 2-KLG wherein said mutant form differs in amino acid sequence from (SEQ ID NO: 1) a wild-type form of a 2,5-DKG reductase enzyme obtained from *Corynebacterium sp.* ATCC strain No. 31090, by:

(A) the replacement of an amino acid residue selected from the group consisting of residues 2, 5, 7, 55, 57, 165, 166, 167, 168, 187, 188, 189, 190, 191, 192, 193, 194, 195, 196, 197, 198, 224, 225, 226, 227, 228, 229, 230, 231, 232, 233, 234, 262, 263, 264, 265, 266, 267, 268, 269, 270, 271, 272, 273, 274, 275, 276, 277 and 278 of said wild-type enzyme or (B) the deletion of an amino acid residue selected from the group consisting of residues 2, 5, 7, 165, 166, 167, 168, 187, 188, 189, 190, 191, 192, 193, 194, 195, 196, 197, 198, 224, 225, 226, 227, 228, 229, 230, 231, 232, 233, 234, 262, 263, 264, 265, 266, 267, 268, 269, 270, 271, 272, 273, 274, 275, 276, 277 and 278 of said wild-type enzyme.

2. The mutant according to claim 1 wherein said replacement is of an amino acid residue at a position selected from the group consisting of 165, 166, 167, 168, 187, 188, 189, 190, 191, 192, 193, 194, 195, 196, 197, 198, 224, 225, 226, 227, 228, 229, 230, 231, 232, 233, 234, 262, 263, 264, 265, 266, 267, 268, 269, 270, 271, 272, 273, 274, 275, 276, 277, and 278 and wherein said deletion is of an amino acid residue at a position selected from the group consisting of 165, 166, 167, 168, 187, 188, 189, 190, 191, 192, 193, 194, 195, 196, 197, 198. 224, 225, 226, 227, 228, 229, 230, 231, 232, 233, 234, 262, 263, 264, 265, 266, 267, 268, 269, 270, 271, 272, 273, 274, 275, 276, 277, and 278.

3. The mutant according to claim 1 having an amino acid substitution in position 192.

4. The mutant according to claim 3 having an arginine at position 192.

5. The mutant form of 2,5-DKG reductase A of claim 1, wherein said mutant form differs in amino acid sequence from a wild-type form of a 2,5-DKG reductase enzyme obtained from *Corynebacterium sp.* ATCC strain No. 31090, by the replacement of an amino acid residue selected from the group consisting of residues 2, 5, and 7 of said wild-type enzyme, and wherein promoter-directed expression, in Acetobacter strain ATCC 39140, of DNA encoding said mutant form causes said mutant form to be accumulated to an even greater extent than that to which wild-type 2,5 DKG reductase A form is accumulated when DNA encoding said wild-type form is expressed directed by said promoter in said Acetobacter strain.

6. The mutant according to claim 5 having an asparagine at position 2, a threonine at position 5, and a serine at position 7.

7. The mutant form of 2,5-DKG reductase A of claim 1, wherein said mutant form has improved temperature stability, and wherein said mutant form differs in amino acid sequence from a wild-type form of a 2,5-DKG reductase enzyme obtained from *Corynebacterium sp.* ATCC strain No. 31090, by the replacement of an amino acid residue selected from the group consisting of residues 55, and 57 of said wild-type enzyme.

8. The mutant according to claim 7 having an alanine at positions 55 and 57.

9. The mutant form of 2,5-DKG reductase A of claim 5, having improved temperature stability, wherein said mutant form additionally differs in amino acid sequence from a wild-type form of a 2,5-DKG reductase enzyme obtained from *Corynebacterium sp.* ATCC strain No. 31090, by the replacement of an amino acid selected from the group consisting of residues 55 and 57 of said wild-type enzyme.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
      ( A ) LENGTH: 278 amino acids
      ( B ) TYPE: amino acid
      ( D ) TOPOLOGY: linear ( i i ) MOLECULE TYPE: protein ( x i ) SEQUENCE DESCRIPTION: SEQ ID NO:1:

```
Met Thr Val Pro Ser Ile Val Leu Asn Asp Gly Asn Ser Ile Pro Gln
 1               5                  10                  15

Leu Gly Tyr Gly Val Phe Lys Val Pro Pro Ala Asp Thr Gln Arg Ala
            20                  25                  30

Val Glu Glu Ala Leu Glu Val Gly Tyr Arg His Ile Asp Thr Ala Ala
        35                  40                  45

Ile Tyr Gly Asn Glu Glu Gly Val Gly Ala Ala Ile Ala Ala Ser Gly
    50                  55                  60

Ile Ala Arg Asp Asp Leu Phe Ile Thr Thr Lys Leu Trp Asn Asp Arg
65                  70                  75                  80

His Asp Gly Asp Glu Pro Ala Ala Ala Ile Ala Glu Ser Leu Ala Lys
                85                  90                  95

Leu Ala Leu Asp Gln Val Asp Leu Tyr Leu Val His Trp Pro Thr Pro
            100                 105                 110

Ala Ala Asp Asn Tyr Val His Ala Trp Glu Lys Met Ile Glu Leu Arg
        115                 120                 125

Ala Ala Gly Leu Thr Arg Ser Ile Gly Val Ser Asn His Leu Val Pro
    130                 135                 140
```

```
His  Leu  Glu  Arg  Ile  Val  Ala  Ala  Thr  Gly  Val  Val  Pro  Ala  Val  Asn
145            150                      155                           160

Gln  Ile  Glu  Leu  His  Pro  Ala  Tyr  Gln  Gln  Arg  Glu  Ile  Thr  Asp  Trp
              165                      170                           175

Ala  Ala  Ala  His  Asp  Val  Lys  Ile  Glu  Ser  Trp  Gly  Pro  Leu  Gly  Gln
              180                 185                           190

Gly  Lys  Tyr  Asp  Leu  Phe  Gly  Ala  Glu  Pro  Val  Thr  Ala  Ala  Ala  Ala
         195                      200                      205

Ala  His  Gly  Lys  Thr  Pro  Ala  Gln  Ala  Val  Leu  Arg  Trp  His  Leu  Gln
    210                      215                 220

Lys  Gly  Phe  Val  Val  Phe  Pro  Lys  Ser  Val  Arg  Arg  Glu  Arg  Leu  Glu
225                      230                 235                           240

Glu  Asn  Leu  Asp  Val  Phe  Asp  Phe  Asp  Leu  Thr  Asp  Thr  Glu  Ile  Ala
              245                      250                           255

Ala  Ile  Asp  Ala  Met  Asp  Pro  Gly  Asp  Gly  Ser  Gly  Arg  Val  Ser  Ala
              260                      265                           270

His  Pro  Asp  Glu  Val  Asp
         275
```

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGCGAAGCTG GCTCTAGATC AGGTCGAC                                28

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATCGTGGGGG CCCCTCGGTC AGGGC                                  25

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GAGGTCGACT GAGGTACCCG AACACCCG                                28

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:5:

GCCCCTCGGT CGCGGCAAGT ACG                                                                             23

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AATTCTATGA ACGTTCCCAC CATCAGCCTC AACGAC                                                               36

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GAAACGAAGA AGCGGTCGCG GCCGCGATCG CG                                                                   32

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGGGCCGCTC GCCCAGGGCA AGT                                                                             23

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CCGCTCGGTC AGAAGTACGA CCT                                                                             23

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGGTCAGGGC CGCTACGACC TCT 23

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TCAGGGCAAG TCGGACCTCT TCG 23

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GCTGCACCCC TACTACCAGC AGC 23

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCACCCCGCC TTCCAGCAGC GCG 23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CCCCGCCTAC CCGCAGCGCG AGA 23

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GCACCTGCAG CTCGGTTTCG TGG 23

(2) INFORMATION FOR SEQ ID NO:16:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:16:

GCAGAAGGGT TCGGTGGTCT TCC                                                   23

(2) INFORMATION FOR SEQ ID NO:17:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:17:

GAAGGGTTTC ACCGTCTTCC CGA                                                   23

(2) INFORMATION FOR SEQ ID NO:18:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:18:

GGGTTTCGTG CCCTTCCCGA AGT                                                   23

(2) INFORMATION FOR SEQ ID NO:19:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:19:

GGGTCGCGTG TGAGCACACC CCG                                                   23